(12) United States Patent
Roh et al.

(10) Patent No.: US 6,916,844 B2
(45) Date of Patent: Jul. 12, 2005

(54) HYDROXY PYRANONE DERIVATIVE AND PREPARATION METHOD THEREOF

(75) Inventors: Ho Sik Roh, Uiwang-shi (KR); Su Nam Kim, Suwon-shi (KR); Bae Hwan Kim, Suwon-shi (KR); Hae Kwang Lee, Yongin-shi (KR); Duck Hee Kim, Seoul (KR); Ih Seop Chang, Yongin-shi (KR); Ok Sub Lee, Anyang-shi (KR)

(73) Assignee: Amorepacific Corporation, Seoul (KR)

( * ) Notice: Subject to any disclaimer, the term of this patent is extended or adjusted under 35 U.S.C. 154(b) by 0 days.

(21) Appl. No.: 10/434,474

(22) Filed: May 9, 2003

(65) Prior Publication Data

US 2003/0236299 A1 Dec. 25, 2003

(30) Foreign Application Priority Data

Jun. 22, 2002 (KR) .................. 10-2002-0035146

(51) Int. Cl.⁷ .................. A61K 31/335; C07D 319/14; C07D 315/00

(52) U.S. Cl. .................. 514/452; 514/460; 549/362; 549/416

(58) Field of Search .................. 549/362, 416; 514/452, 460

(56) References Cited

U.S. PATENT DOCUMENTS 5,523,421 A * 6/1996 Yang et al. .................. 549/418

* cited by examiner

*Primary Examiner*—Cecilia J. Tsang
*Assistant Examiner*—Raymond Covington
(74) *Attorney, Agent, or Firm*—Nixon & Vanderhye P.C.

(57) ABSTRACT

The present invention provides hydroxy pyranone derivatives and a method for preparing the hydroxy pyranone derivatives. The hydroxy pyranone derivatives of the present invention are significantly effective in promoting the biosynthesis of collagen and in inhibiting the activity of collagenase, i.e. an enzyme for decomposing collagen, to have anti-wrinkle efficacy, and can be incorporated into medicines or external applications for lessening skin-wrinkles.

7 Claims, No Drawings

HYDROXY PYRANONE DERIVATIVE AND PREPARATION METHOD THEREOF

FIELD OF THE INVENTION

The present invention relates to a novel hydroxy pyranone derivative represented by the following formula 1 and to a preparation method thereof:

[Formula 1]

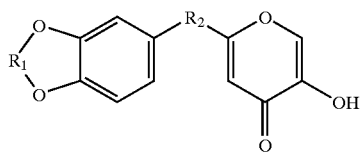

(wherein, $R_1$ is —$CH_2$— or —$CH_2CH_2$—; and $R_2$ is —C(O)OCH$_2$—, —CH=CHC(O)OCH$_2$— or —CH=CH—).

BACKGROUND OF THE INVENTION

The skin of a living thing becomes aged as it grows older. In order to delay this skin aging, extensive efforts have been made, and the questions of what is the essence of skin aging and why does the skin become aged have been successively brought up. Generally, skin aging is classified into two classes depending on its cause.

The first is intrinsic aging, that is, the structure and the physiological function of the skin deteriorate as it ages. The second is extrinsic aging, which is caused by accumulated stresses such as UV radiation. Particularly, UV radiation is a well-known cause of aging. In case when skin is radiated under UV for a long time, the stratum corneum of skin becomes thicker and collagen is denatured and thereby skin loses its elasticity. Thus, skin aging is accompanied by several functional, and structural changes.

As the structural changes caused by skin aging, the epidermis, dermis and hypoderm of the skin become thinner. In addition, dermal ECM (extracellular matrix), which takes charge of skin elasticity and elongation, is deteriorated because the components of the ECM denatured. ECM is mainly composed of two components, i.e. about 2~4% of elastic fiber and about 70~80% of collagen. In the process of skin aging, the collagen production reduces rapidly, and this reduction is caused by several factors in biosynthesis. For example, a matrix metallo protease such as collagenase is activated to decompose collagen, resulting in the reduction of collagen in the skin. The reduction of collagen in the dermis of skin causes the skin to become rough and wrinkled, that is, the skin becomes aged.

In order to suppress the collagen-reduction, which is a cause of wrinkling, some materials have been developed for use. Specially, retinoids such as retinol and retinoic acid have been known to be very effective in lessening skin wrinkles. (*Dermatology therapy*, 1998, 16, 357~364)

In spite of anti-wrinkle efficacy, retinoids have some drawbacks in that they cause irritation to the skin with a small quantity and they are easily oxidized in the air due to their instability, so that they are limited in utilization. In order to stabilize retinoids, many studies have been made, however, the irritation of retinoid to the skin has not yet been fully solved. That is, problems in the safety on the skin remain unsolved.

Retinoids include retinol, retinoic acid and their derivatives. They exhibit various biological activities, and as an example involved in the skin, the effects on abnormal keratinization or on pimple were reported. Also, concerning their involvement in skin wrinkles, it is that they can promote the biosynthesis of collagen and inhibit the activity of collagenase, i.e. an enzyme for decomposing collagen (*The Journal of Investigative Dermatology*, 1991, 96, 975~978).

Up to now, retinoids have been developed as follows: In the first stage, simple derivatives of retinol or retinoic acid were developed, and as such derivative, there is a retinyl palmitate. In the next stage, a retinoid derivative prepared by using benzoic acid named arotinoid was developed (*J. Med. Chem*, 1988, 31, 2182~2192). Recently, a compound called heteroarotinoid has been developed, in which a heteroatom is introduced into the benzene ring of the arotinoid (*J. Med. Chem.*, 1999, 42, 4434~4445). The present invention provides a retinoid derivative including hydroxy pyranone, instead of benzoic acid having a heteroatom.

Retinoids are reported to exhibit a biological effect on the skin by acting with an intercellular receptor called a retinoic receptor (*British Journal of dermatology*, 1999, 140, 12~17). The structural features of retinoids are resulted from tetramethyl cyclohexane, unsaturated carbon bonds and carboxylic acid. In particular, carboxylic acid moiety is an essential part, which can be easily transformed into anion when the retinoids are acting with the receptor (*Chem. Pharm. Bull*, 2001, 49, 501~503).

Based on the above results, researches have been made to lessen toxicity, irritation and instability of the retinoid derivatives while maintaining their intrinsic effects.

Under this circumstance, the present inventors have studied to find a novel type of retinoid that having reduced skin irritation and increased stability in the external formulation for skin care, and invented a desired type of retinoid.

In addition, 5-hydroxy-2-(hydroxymethyl)-4H-pyrane-4-one and its derivatives are known as skin-whitening agents. (U.S. Pat. No. 5,523,421; *Bioorganic & Medicinal chemistry letter*, 1996, 6, 1303~1308). In addition to its whitening efficacy, 5-hydroxy-2-(hydroxymethyl)-4H-pyrane-4-one is reported to be very effective in inhibiting skin wrinkle (*European Journal of Pharmacology*, 2001, 411, 169~174).

Considering of structural feature, 5-hydroxy-2-(hydroxymethyl)-4H-pyrane-4-one has a 4-positioned carbonyl group and a 5-positioned enolic hydroxy group. The enolic hydroxy group can be easily transformed into anion, to be used in the form of carboxylic acid. In the present invention, this structural feature of 5-hydroxy-2-(hydroxymethyl)-4H-pyrane-4-one was used in synthesizing novel retinoid. The present inventors found that a novel retinoid, i.e. a novel 5-hydroxy-2-(hydroxymethyl)-4H-pyrane-4-one derivative synthesized in the present invention, have excellent safety to the skin and improved stability in the formulations. That is, the retinoid of the present invention does not cause skin irritation, discoloration and odorizing. Based on this finding, the present invention has been completed.

Therefore, an object of the invention is to provide a novel hydroxy pyranone derivative as a novel type of retinoid, which can prevent skin wrinkle and has excellent safety to the skin and improved stability in the formulations.

Another object of the present invention is to provide a method for preparing the hydroxy pyranone derivative.

A further object of the present invention is to show compatibility of the hydroxy pyranone derivative to medicines or external applications for skin care.

SUMMARY OF THE INVENTION

In order to accomplish said objects, the present invention provides, as a novel retinoid, a hydroxy pyranone derivative represented by the following formula 1:

[Formula 1]

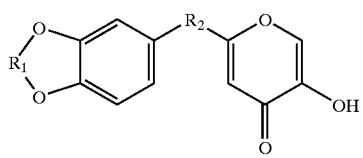

(wherein, R₁ is —CH₂— or —CH₂CH₂—; and R₂ is —C(O)OCH₂—, —CH=CHC(O)OCH₂— or —CH=CH—).

Further, the present invention provides a method for forming ester bond between 5-hydroxy-2-(hydroxymethyl)-4H-pyrane-4-one and one selected from the group consisting of 3,4-methylene dioxybenzoic acid, 3,4-ethylene dioxybenzoic acid, 3,4-methylene dioxycinnamic acid and 3,4-ethylene dioxycinnamic acid; and provides a method for connecting 5-hydroxy-2-(hydroxymethyl)-4H-pyrane-4-one with 3,4-methylene dioxybenzaldehyde or 3,4-ethylene dioxybenzaldehyde via a double bond.

Considering the structure and effects, the hydroxy pyranone derivative represented by the formula 1 of the present invention can be classified as a retinoid.

Hereinafter, the present invention is described in detail.

DETAILED DESCRIPTION OF THE INVENTION

The hydroxy pyranone derivative as a novel retinoid of the present invention may be prepared by either of two methods exemplified as follows:

The first method (A) may comprise the steps of: substituting halogen for hydroxy group of 2-hydroxymethyl-position of 5-hydroxy-2-(hydroxymethyl)-4H-pyrane-4-one to prepare 5-hydroxy-2-(halogenmethyl)-4H-pyrane-4-one; reacting benzoic acid or cinnamic acid with inorganic base in a polar solvent to prepare benzoate or cinnamate; and reacting said 5-hydroxy-2-(halogenmethyl)-4H-pyrane-4-one and said benzoate or cinnamate to produce hydroxy pyranone derivative.

The second method (B) may comprise the steps of: substituting halogen for hydroxy group of 2-hydroxymethyl-position of 5-hydroxy-2-(hydroxymethyl)-4H-pyrane-4-one to prepare 5-hydroxy-2-(halogenmethyl)-4H-pyrane-4-one; reacting said 5-hydroxy-2-(halogenmethyl)-4H-pyrane-4-one with triphenyl phosphine to form phosphonium salt; and reacting said phosphonium salt with 3,4-methylene dioxybenzaldehyde or 3,4-ethylene dioxybenzaldehyde to produce hydroxy pyranone derivative.

In the above two methods, halogen may be bromine, chlorine or iodine.

The methods of the present invention will be described in more detail by the following reaction schemes.

First, the method (A) may be exemplified by the following reaction scheme 1, for example:

[Reaction Scheme 1]

Method A

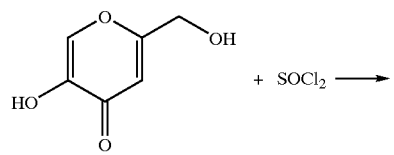

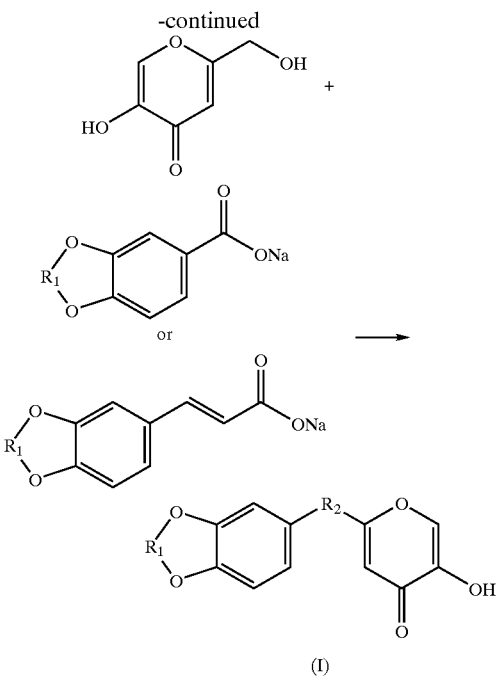

(wherein, R₁ is —CH₂— or —CH₂CH₂—; and R₂ is —C(O)OCH₂— or —CH=CHC(O)OCH₂—).

As a first step, the primary alcohol of 5-hydroxy-2-(hydroxymethyl)-4H-pyrane-4-one may be transformed into chloride by employing thionyl chloride. A solvent employed in this step may be N,N-dimethylformamide, methylene chloride, chloroform or the like. As a second step, benzoic acid or cinnamic acid may be transformed into their salts by employing an inorganic base such as sodium hydroxide, potassium hydroxide or the like, and as a solvent, a polar solvent such as methanol, ethanol, dioxane, tetrahydrofuran and the like may be employed in this step.

As a third step, 5-hydroxy-2-(chloromethyl)-4H-pyrane-4-one prepared by transforming the primary alcohol into chloride in the first step may be reacted with benzoate or cinnamate prepared in the second step in a solvent such as N,N-dimethylformamide, methylene chloride, chloroform or the like. More preferably, it may be N,N-dimethylformamide. The reaction may be preferably performed at a temperature of 70~110° C. If the temperature is lower than 70° C., 5-hydroxy-2-(chloromethyl)-4H-pyrane-4-one may remain unreacted and then is difficult to be removed from the product. If the temperature is higher than 110° C., 5-hydroxy-2-(chloromethyl)-4H-pyrane-4-one may be decomposed, resulting in reducing the yield of the product.

Further, the method (B) may be exemplified by the following reaction scheme 2, for example:

[Reaction Scheme 2]

Method B

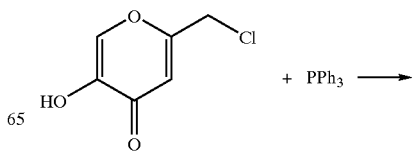

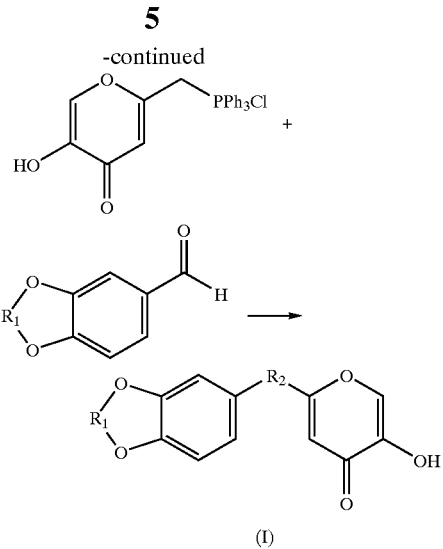

(wherein, R₁ is —CH₂— or —CH₂CH₂—; and R₂ is —CH=CH—).

At first, 5-hydroxy-2-(chloromethyl)-4H-pyrane-4-one as is prepared in the first step of method (A) may be reacted with triphenyl phosphine to obtain phosphonium salt. A solvent employed in this reaction may be methylene chloride, chloroform, dioxane, tetrahydrofuran, benzene, toluene or the like.

Then, the phosphonium salt may be reacted with a base, to obtain an ylide, and as a base, n-BuLi, sodium methoxide, sodium ethoxide, or the like may be employed. The ylide obtained above may be reacted with aldehyde to produce a stilbene compound.

In the two methods exemplified above, instead of thionyl chloride, thionyl bromide may be employed to obtain 5-hydroxy-2-(bromomethyl)-4H-pyrane-4-one. Also, 5-hydroxy-2-(iodomethyl)-4H-pyrane-4-one can be obtained by reacting the 5-hydroxy-2-(chloromethyl)-4H-pyrane-4-one with sodium iodide or potassium iodide. The above reactions may also be proceeded by employing 5-hydroxy-2-(bromomethyl)-4H-pyrane-4-one or 5-hydroxy-2-(chloromethyl)-4H-pyrane-4-one.

The 5-hydroxy-2-(hydroxymethyl)-4H-pyrane-4-one ester, stilbene compound of the formula 1 obtained by the above methods may include, but not limited thereto, (5-hydroxy-4-oxo-4H-pyran-2-yl) methyl 2H-benzo [3,4-d] 1,3-dioxolan-5-carboxylate;

(5-hydroxy-4-oxo-4H-pyran-2-yl) 2H,3H-benzo [3,4-e] 1,4-dioxane-6-carboxylate;

2-((3E)-4-(2H,3H-benzo [3,4-d] 1,3-dioxolan-5-yl)-2-oxobut-3-enyloxy)-5hydroxy-4-pyran-4-one;

2-((3E)-4-(2H,3H-benzo [3,4-e] 1,4-dioxan-6-yl)-2-oxobut-3-enyloxy)-5hydroxy-4-pyran-4-one;

2-((1E)-2-(2H,3H-benzo [3,4-d] 1,3-dioxolan-5-yl) vinyl)-5-hydroxy-4H-pyran-4-one;

2-((1E)-2-(2H,3H-benzo [3,4-e] 1,4-dioxan-6-yl)vinyl)-5-hydroxy-4H-pyran-4-pyran-4-one; or the like.

The 5-hydroxy-2-(hydroxymethyl)-4H-pyrane-4-one ester, stilbene compound of the formula 1 obtained in the above methods may be incorporated into the compositions for medicines or external applications for lessening skin-wrinkles.

The composition of the present invention may further incorporate other conventional ingredients depending on the formulation. In addition to the hydroxy pyranone derivative, the present composition may further comprise other conventional anti-wrinkle agents for the purpose of lessening skin-wrinkles.

PREFERRED EMBODIMENT OF THE INVENTION

The preparation of the 5-hydroxy-2-(hydroxymethyl)-4H-pyrane-4-one ester, stilbene compounds will be described in more detail by way of the following examples, which should not be considered to limit the scope of the present invention.

PREPARATION EXAMPLE 1

Preparation of 5-hydroxy-2-(chloromethyl)-4H-pyran-4-one 50 g (0.35 mol) of 5-hydroxy-2-(hydroxymethyl)-4H-pyrane-4-one was dissolved in 250 ml of N,N-dimethylformamide and then was cooled in an ice bath at 10° C. Thereto, 50 ml (0.42 mol) of thionyl chloride was added drop by drop for 30 minutes. The mixture was stirred at a room temperature for 2 hours and then added to 2000 ml of ice water. The obtained solid material was filtered and then dissolved in 1000 ml of ethyl acetate. The product was dried over magnesium sulfate, decolorized with active charcoal and then filtered. The filtrate was concentrated and hexane was added thereto to obtain crystals. The recovered crystals were dried under vacuum to obtain 39.5 g (yield: 70%) of the desired product, i.e., 5-hydroxy-2-(chloromethyl)-4H-pyran-4-one as a yellow solid state.

PREPARATION EXAMPLE 2

Preparation of 5-hydroxy-2-(chloromethyl)-4H-pyran-4-onyl Triphenyl Phosphorane 30 g (0.18 mol) of 5-hydroxy-2-(chloromethyl)-4H-pyran-4-one was dissolved in 500 ml of methylene chloride. Thereto, 49 g (0.18 mol) of triphenyl phosphine was added and then refluxed for 6 hours. During the reflux, solid was obtained. After the reaction, the obtained solid was filtered, to obtain 63 g (yield: 75%) of phosphonium salt.

EXAMPLE 1

Preparation of (5-hydroxy-4-oxo-4H-pyran-2-yl) methyl 2H-benzo [3,4-d] 1,3-dioxolan-5-carboxylate (Method A)

5 g (0.03 mol) of 3,4-methylene dioxybenzoic acid and 1.8 g (0.45 mol) of sodium hydroxide were dissolved in 40 ml of methanol, then after distilling the methanol, the residue was dissolved in 70 ml of N,N-dimethylformamide. Then, 4.8 g (0.03 mol) of 5-hydroxy-2-(chloromethyl)-4H-pyran-4-one was added thereto, and the resulting mixture was heated with stirring for 2 hours in an oil bath at 110° C. After distilling out solvent, the residue was dissolved in 300 ml of ethyl acetate. The ethyl acetate solution was washed with 5% hydrochloric acid and distilled water, dried over magnesium sulfate, decolorized with active charcoal and then filtered. The filtrate was dried and concentrated under reduced pressure to obtain 5.6 g (yield: 65%) of the desired product as a pale yellow solid.

TLC (in ethyl acetate:hexane=1:1) Rf=0.54 $^1$H-NMR (DMSO, δ); 9.43(S, 1H), 8.16(S, 1H), 7.69(d, 1H, J=8.4 Hz), 7.48(S, 1H), 7.12(d, 1H, J=8.4 Hz), 6.60(S, 1H), 6.20(S, 2H), 5.22(S, 2H).

EXAMPLE 2

Preparation of (5-hydroxy-4-oxo-4H-pyran-2-yl) 2H,3H-benzo [3,4-e] 1,4-dioxane-6-carboxylate Instead of 3,4-methylene dioxybenzoic acid, the procedure described in Example 1 was followed by employing 3,4-ethylene dioxybenzoic acid, to obtain 6.2 g (yield: 68%) of the desired product as a pale yellow solid.

TLC (in ethyl acetate:hexane=1:2) Rf=0.53 $^1$H-NMR (DMSO, δ); 9.42(S, 1H), 8.15(S, 1H), 7.65(d, 1H, J=8.4 Hz), 7.49(S, 1H), 7.10(d, 1H, J=8.4 Hz), 6.63(S, 1H), 6.18(S, 2H), 4.27(S, 2H).

EXAMPLE 3

Preparation of ((3E)-4-(2H,3H-benzo [3,4-d] 1,3-dioxolan-5-yl)-2-oxobut-3-enyloxy)-5-hydroxy-4H-pyran-4-one Instead of 3,4-methylene dioxybenzoic acid, the procedure described in Example 1 was followed by employing 3,4-methylene dioxycinnamic acid, to obtain 5.8 g (yield: 62%) of the desired product as a pale yellow solid.

TLC (in ethyl acetate:hexane=1:4) Rf=0.50 $^1$H-NMR (DMSO, δ); 9.40(S, 1H), 8.09(S, 1H), 7.63(d, 2H, J=15.9 Hz), 7.44(S, 1H), 7.21(d, 1H, J=8.47 Hz), 6.95(d, 1H, 8.4 Hz), 6.61(d, 1H, J=15.9 Hz), 6.50(S, 1H), 6.07(S, 2H), 5.05(S, 2H).

EXAMPLE 4

Preparation of 2-((3E)-4-(2H,3H-benzo [3,4-e] 1,4-dioxan-6-yl)-2-oxobut-3

Instead of 3,4-methylene dioxybenzoic acid, the procedure described in Example 1 was followed by employing 3,4-ethylene dioxycinnamic acid, to obtain 5.9 g (yield: 60%) of the desired product as a pale yellow solid.

TLC (in ethyl acetate:hexane=1:4) Rf=0.51 $^1$H-NMR (DMSO, δ); 9.39(S, 1H), 8.09(S, 1H), 7.62(d, 1H, J=15.9 Hz), 7.16(S, 1H), 7.02(d, 1H, J=8.47 Hz), 6.82(d, 1H, 8.4 Hz), 6.59(d, 1H, J=15.9 Hz), 6.50(S, 1H), 5.06(S, 2H), 4.30(m, 2H).

EXAMPLE 5

Preparation of 2-((1E)-2-(2H,3H-benzo [3,4-d] 1,3-dioxolan-5-yl) vinyl)-5-hydroxy-4H-pyran-4-one (Method B)

20 g (0.047 mol) of phosphonium salt was dissolved in 200 ml of anhydrous tetrahydrofuran and then cooled to a temperature of 0° C. Thereto, 19 ml (0.047 mol) of 2.5M n-BuLi was gradually added. The reaction solution was stirred for another 30 minutes. 7 g (0.047 mol) of 3,4-methylene dioxybenzaldehyde was dissolved in 50 ml of anhydrous tetrahydrofuran and then added to the above solution drop by drop. After reaction, the reaction solution was concentrated and then dissolved in 100 ml of ethyl acetate. The ethyl acetate solution was washed with distilled water twice, dried over anhydrous sodium sulfate and then filtered. The filtrate was concentrated and then subjected to column chromatography, to obtain 7.2 g (yield: 60%) of the desired product as a pale yellow solid.

TLC (in ethyl acetate:hexane=1:4) Rf=0.50 $^1$H-NMR (CDCl$_3$, δ); 9.12(s, 1H), 8.02(s, 1H), 7.28–7.32(m, 2H), 7.14(d, 1H J=7.8 Hz), 6.97(s, 1H), 6.90(d, 1H, J=14.5 Hz), 6.41(s, 1H), 6.41(s, 2H).

EXAMPLE 6

Preparation of 2-((1E)-2-(2H,3H-benzo [3,4-e] 1,4-dioxan-6-yl) vinyl)-5-hydroxy-4H-pyran-4-one Instead of 3,4-methylene dioxybenzaldehyde, the procedure described in Example 5 was followed by employing 3,4-ethylene dioxybenzaldehyde, to obtain 7.8 g (yield: 61%) of the desired product as a pale yellow solid.

TLC (in ethyl acetate:hexane=1:4) Rf=0.51 $^1$H-NMR (CDCl$_3$, δ); 9.10(s, 1H), 8.02(s, 1H), 7.29(d, 1H, J=16.2 Hz), 7.20(s, 1H), 7.13(m, 1H), 6.91(m, 2H), 6.43(s, 1H), 4.26(m, 4H).

EXPERIMENTAL EXAMPLE 1

Effect on Biosynthesis of Collagen

The effect of the hydroxy pyranone derivatives obtained in Examples 1~6 on biosynthesis of collagen was compared with those of retinol and retinoic acid.

Human fibroblasts were seeded into a 24-well plate to a density of $10^5$ cells/well and then cultured to 90% of growth. The plate was washed with PBS (phosphate buffered saline) and treated with test samples at a concentration of $10^{-4}$M, and then incubated in a $CO_2$ incubator for 24 hours. From its supernatant, procollagen production was measured with procollagen type (I) ELISA kit. The results are shown in Table 1. The biosynthesis of collagen was evaluated as a relative value compared with that of the control group, which is not treated with sample and of which the value of biosyntheis of collagen was set to be 100.

TABLE 1

| Test samples | Biosynthesis of collagen (%) |
| --- | --- |
| Control group | 100 |
| Retinol | 120 |
| Retinoic acid | 125 |
| Compound of Ex. 1 | 118 |
| Compound of Ex. 2 | 121 |
| Compound of Ex. 3 | 123 |
| Compound of Ex. 4 | 122 |
| Compound of Ex. 5 | 116 |
| Compound of Ex. 6 | 115 |

EXPERIMENTAL EXAMPLE 2

Collagenase-Inhibiting Effect

The collagenase-inhibiting effect of hydroxy pyranone derivatives obtained in Examples 1~6 was compared with those of retinol and retinoic acid.

Human fibroblasts were cultured in Dulbecco's Modified Eagle's Medium (DMEM) supplemented with 2.5% fetal bovine serum. The fibroblasts were seeded into a 96-well microtiter plate to a density of 5,000 cells/well, and then cultured to 70~80% of growth. The plate was treated with test samples at a concentration of $10^{-4}$M for 24 hours, then the cultured medium and the cells were raked up and recovered. From the recovered culture, collagenase production was measured with collagenase kit (Catalog #: RPN 2610) commercialized by Amersham Pharmacia Biotech. First, the recovered culture was added into a 96-well plate wherein primary collagenase antibodies were uniformly spread, and then antigen-antibody reaction was performed in an incubator for 3 hours. Later, secondary collagenase antibodies bonded with chromophore were added to the 96-well plate and reacted for 15 minutes. Then, color former was added thereto in order to induce development at the room temperature for 15 minutes, and 1M of sulfuric acid was added to stop the reaction. The reaction solution became yellow, and the color density depends on the progress of the reaction. The absorbance of the yellow 96-well plate was measured at 405 nm with absorptiometer. The expression of collagenase was calculated by the following equation 1. No sample was treated in the control group.

[Equation 1]

The expression of collagenase (%)=[(Absorbance of test group)/(Absorbance of control group)]×100

As shown in Table 2, the result confirmed that the present compounds could inhibit the expression of collagenase in vitro. The expression of collagenase was evaluated as a relative value compared with that of the control group of which the expression of collagenase was set to be 100.

TABLE 2

| Test samples | Expression of collagenase (%) |
| --- | --- |
| Control group | 100 |
| Retinol | 82 |
| Retinoic acid | 75 |
| Compound of Ex. 1 | 83 |
| Compound of Ex. 2 | 81 |
| Compound of Ex. 3 | 78 |
| Compound of Ex. 4 | 77 |
| Compound of Ex. 5 | 88 |
| Compound of Ex. 6 | 84 |

EXPERIMENTAL EXAMPLE 3

Primary Skin Irritation Test on Animals

This test was performed for six (6) healthy male rabbits whose hairs on both sides of the backs were cut. The compounds of Examples 1~6 were dissolved in 1,3-butylene glycol:ethanol=7:3, to obtain 1% concentration of test samples. 0.5 ml of each test samples were applied to right side area of 2.5 cm×2.5 cm. No sample was treated on left side as a control. 24 hours and 72 hours later, skin abnormality such as erythema, crust and edema was observed. Skin response was scored according to "standard guide for toxicity test of foods and drugs", as shown in Table 3. Based on the score of skin response, skin irritation was estimated according to Draize's P.I.I. (Primary Irritation Index) and compared with that of retinoic acid. The results are shown in Table 4.

TABLE 3

| | Skin responses | Score |
| --- | --- | --- |
| 1) Erythema and crust | No erythema | 0 |
| | Slight erythema (scarcely visible) | 1 |
| | Significant erythema | 2 |
| | Severe erythema | 3 |
| | Crimson extremely-severe erythema and crust | 4 |
| 2) Edema | No edema | 0 |
| | A slight edema (scarcely visible) | 1 |
| | Significant edema (distinct from periphery) | 2 |
| | Severe edema (swelled up about 1 mm) | 3 |
| | Extremely-severe edema (swelled up 1 mm or more and expanded out of the exposed site) | 4 |

TABLE 4

| Test samples | P. I. I. | Evaluation |
| --- | --- | --- |
| Retinoic acid | 1.830 | Light irritation |
| Compound of Ex. 1 | 0.375 | No irritation |
| Compound of Ex. 2 | 0.345 | No irritation |
| Compound of Ex. 3 | 0.375 | No irritation |
| Compound of Ex. 4 | 0.350 | No irritation |

TABLE 4-continued

| Test samples | P. I. I. | Evaluation |
| --- | --- | --- |
| Compound of Ex. 5 | 0.375 | No irritation |
| Compound of Ex. 6 | 0.315 | No irritation |

As shown in Table 4, the compounds of Examples 1~6 were confirmed to be non-irritable to the skin.

This non-irritation effect is superiority of the novel retinoid invented in the present invention. That is, the hydroxy pyranone derivatives of the present invention have the same anti-wrinkle efficacy as that of retinol or retinoic acid but have superior safety and less irritation.

EXPERIMENTAL EXAMPLE 4

Phototoxicity Test

This test was performed for ten (10) white guinea pigs whose hairs on both sides of the backs were cut, and fixed. On the back of the guinea pig, six (6) test sites measuring 2.5 cm×2.5 cm, three (3) per each side, were sectioned. Right sites were prepared as controls with no irradiation (UV non-irradiation sites) and left sites were irradiated (UV irradiation sites). Vehicle (1,3-butylene glycol:ethanol=7:3) was used as a negative control, and 0.1% concentration of 8-MOP (methoxypsoralene) was used as a positive control; and 1% (w/v) solutions of the compounds of Examples 1~6 were applied to either site with an amount of 50 ml for each site. 30 minutes later, right sites were shielded with aluminum foil and UVA(320~380 nm) was irradiated at a distance of about 10 cm therefrom with Waldmann to the final energy of 15 J/cm$^2$. After 24, 48 and 72 hours elapsed, skin response of guinea pig was observed. Erythema and edema were scored from 0 to 4 points as shown in the Table 3, and skin response was evaluated by summing the scores. Maximum scores were selected when measured on each elapsed time, i.e. 24, 48 and 72 hours, and irritation index was calculated according to the following equation 2. Then, phototoxic index was calculated according to the following equation 3. The results are shown in Table 5.

[Equation 2]

Irritation index=(Maximum of erythema+Maximum of edema)/Number of animals

[Equation 3]

Phototoxic index=(Irritation index of UV irradiation site)−(Irritation index of UV non-irradiation site)

TABLE 5

| Test samples | Phototoxic index | Evaluation |
| --- | --- | --- |
| Compound of Ex. 1 | 0 | No phototoxicity |
| Compound of Ex. 2 | 0 | No phototoxicity |
| Compound of Ex. 3 | 0 | No phototoxicity |
| Compound of Ex. 4 | 0 | No phototoxicity |
| Compound of Ex. 5 | 0 | No phototoxicity |
| Compound of Ex. 6 | 0 | No phototoxicity |

As shown in Table 5, it was confirmed that phototoxic indexes of the compounds of Examples 1~6 were 0, which is a lower value than 0.5, the criterion value to be estimated as no phototoxicity.

EXPERIMENTAL EXAMPLE 5

Ames Test

Reversion mutagenisis assay (Ames test) was conducted by using strains TA98 and TA100 of *Salmonella* as test strains. The result was negative in this test condition, showing that mutations were not induced from the test strains. That is, it was confirmed that the present compounds are not so irritative as to cause mutation even in *Salmonella* strains.

EXPERIMENTAL EXAMPLE 6

Human Patch Test

This test was performed for thirty (30) healthy females and males aged on average 24.8 years and having no experience of hypersensitivity, according to method of CTFA Guideline (The Cosmetic, Toiletry and Fragrance Association. Inc. Washington, D.C., 20023, 1991). Each compound of Examples 1~6 was dissolved in patch base having the composition of Table 6 to be 1% concentration as for test materials, and 20 μl of each test materials was dropped into a Finn chamber respectively, then attached to the forearm of the subject and fixed with a micropore tape. After 24 hours of patching, the patches were removed and the test sites were marked with marking pen. The observations of the test sites were made after 24 and 48 hours from the patching. Skin responses were evaluated as shown in Table 7 and the results are shown in Table 8.

TABLE 6

| Materials | CTFA | Amount |
|---|---|---|
| Oil and wax | Glyceryl stearate | 1.50 |
| | Squalane | 7.00 |
| | Mineral oil | 7.00 |
| | Cetyl alcohol | 1.20 |
| Surfactant | Sorbitan stearate | 0.30 |
| | Polysorbate-60 | 1.00 |
| Thickener | Carbomer | 0.12 |
| Polyol | Glycerin | 10.00 |
| Water | Distilled water | To 100 |

TABLE 7

| Grade | Symbol | Skin responses |
|---|---|---|
| 0 | − | No visible response |
| 1 | ± | Mild erythema |
| 2 | + | Intense erythema |
| 3 | + + | Intense erythema with edema |
| 4 | + + + | Intense erythema with edema and vesicle |

TABLE 8

| | Number of the subjected showing response | | | | | | | | | | Average |
|---|---|---|---|---|---|---|---|---|---|---|---|
| | 24 hours later | | | | | 48 hours later | | | | | Response |
| Test samples | − | ± | + | + + | + + + | − | ± | + | + + | + + + | (n = 30) |
| Compound of Ex. 1 | 28 | 2 | 0 | 0 | 0 | 30 | 0 | 0 | 0 | 0 | 0.83 |
| Compound of Ex. 2 | 30 | 0 | 0 | 0 | 0 | 29 | 1 | 0 | 0 | 0 | 0.42 |
| Compound of Ex. 3 | 30 | 0 | 0 | 0 | 0 | 30 | 0 | 0 | 0 | 0 | 0.00 |
| Compound of Ex. 4 | 29 | 1 | 0 | 0 | 0 | 30 | 0 | 0 | 0 | 0 | 0.42 |
| Compound of Ex. 5 | 30 | 0 | 0 | 0 | 0 | 30 | 0 | 0 | 0 | 0 | 0.00 |
| Compound of Ex. 6 | 30 | 0 | 0 | 0 | 0 | 30 | 0 | 0 | 0 | 0 | 0.00 |

The average response of Table 8 was calculated by the following equation 4.

$$\text{Average response} = \frac{[\text{Sum of } \{\text{Grade of the sample} \times \text{Number of the subjects showing response at that grade}\}]}{[4(\text{Maximum grade}) \times 30(\text{Total number of the subjected}) \times 2(\text{Total number of tests repeated})]} \times 100 \quad [\text{Equation 4}]$$

As shown in Table 8, it was confirmed that average responses to the skin irritation of the anti-wrinkle compositions according to the present invention were 0~0.83, which is lower than the value 1, the criterion value estimated to have no irritation. Therefore, the present compositions are regarded to be safe for applying to the skins of living things.

What is claimed is:

1. Hydroxy pyranone compound represented by the following formula 1:

[Formula 1]

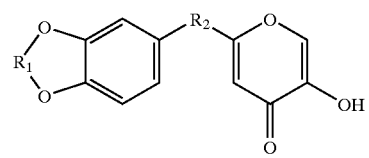

(I)

(wherein, $R_1$ is —$CH_2$— or —$CH_2CH_2$—; and $R_2$ is —$C(O)OCH_2$—, —$CH=CHC(O)OCH_2$— or —$CH=CH$—).

2. A method for preparing hydroxy pyranone compound represented by the following formula 1, comprising the steps of:

[Formula 1]

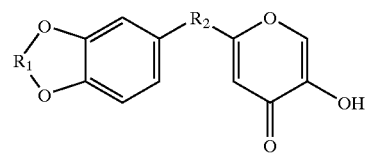

(I)

(wherein, $R_1$ is —$CH_2$— or —$CH_2CH_2$—; and $R_2$ is —$C(O)OCH_2$— or —$CH=CHC(O)OCH_2$—)

(1) substituting halogen for hydroxy group of 2-hydroxymethyl position of 5-hydroxy-2-

(hydroxymethyl)-4H-pyrane-4-one to prepare 5-hydroxy-2-(halogenmethyl)-4H-pyrane-4-one;

(2) reacting benzoic acid or cinnamic acid with inorganic base in a polar solvent to prepare benzoate or cinnamate; and (3) reacting the 5-hydroxy-2-(halogenmethyl)-4H-pyrane-4-one and the benzoate or cinnamate.

3. The method according to claim 2, wherein said halogen is bromine, chlorine or iodine.

4. A method for preparing hydroxy pyranone compound represented by the following formula 1, comprising the steps of:

[Formula 1]

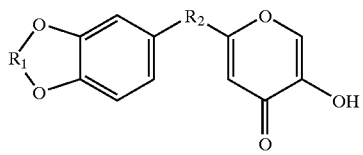

(I)

(wherein, $R_1$ is —$CH_2$— or —$CH_2CH_2$—; and $R_2$ is —CH=CH—), (1) substituting halogen for hydroxy group of 2-hydroxymethyl position of 5-hydroxy-2-(hydroxymethyl)-4H-pyrane-4-one to prepare 5-hydroxy-2-(halogenmethyl)-4H-pyrane-4-one;

(2) reacting the 5-hydroxy-2-(halogenmethyl)-4H-pyrane-4-one with triphenyl phosphine, to prepare phosphonium salt; and (3) reacting the phosphonium salt with 3,4-methylene dioxybenzaldehyde or 3,4-ethylene dioxybenzaldehyde.

5. The method according claim 4, wherein said halogen is bromine, chlorine or iodine.

6. A composition for topical application to skin comprising together with a carrier or diluent a hydroxy pyranone compound represented by the following formula 1:

[Formula 1]

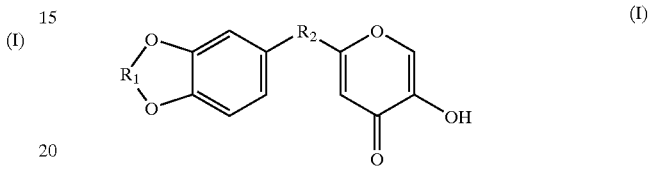

(I)

wherein, $R_1$ is —$CH_2$— or —$CH_2CH_2$—; and $R_2$ is —C(O)O$CH_2$—, CH=CHC(O)O$CH_2$— or —CH=CH—.

7. A method for improving skin wrinkle by applying the hydroxy pyranone compound according to claim 1 to the skin.

* * * * *